(12) United States Patent
Murase et al.

(10) Patent No.: US 12,075,978 B2
(45) Date of Patent: Sep. 3, 2024

(54) BENDING MECHANISM AND MEDICAL EQUIPMENT

(71) Applicant: KAWASAKI JUKOGYO KABUSHIKI KAISHA, Kobe (JP)

(72) Inventors: Yohei Murase, Kobe (JP); Tamami Oryu, Kobe (JP)

(73) Assignee: KAWASAKI JUKOGYO KABUSHIKI KAISHA, Kobe (JP)

( * ) Notice: Subject to any disclaimer, the term of this patent is extended or adjusted under 35 U.S.C. 154(b) by 693 days.

(21) Appl. No.: 17/293,616

(22) PCT Filed: Nov. 19, 2019

(86) PCT No.: PCT/JP2019/045215
§ 371 (c)(1),
(2) Date: May 13, 2021

(87) PCT Pub. No.: WO2020/105616
PCT Pub. Date: May 28, 2020

(65) Prior Publication Data
US 2022/0015609 A1    Jan. 20, 2022

(30) Foreign Application Priority Data
Nov. 22, 2018   (JP) ................................. 2018-219532

(51) Int. Cl.
*A61B 1/01*      (2006.01)
*A61B 17/00*     (2006.01)
*A61B 17/29*     (2006.01)

(52) U.S. Cl.
CPC ...... *A61B 1/01* (2013.01); *A61B 2017/00314* (2013.01); *A61B 2017/00323* (2013.01); *A61B 2017/2905* (2013.01)

(58) Field of Classification Search
CPC ............ A61B 1/01; A61B 2017/00314; A61B 2017/00323; A61B 2017/2905;
(Continued)

(56) References Cited

U.S. PATENT DOCUMENTS 3,060,972 A * 10/1962 Sheldon ............... A61B 1/0055
                                                    138/120
9,517,326 B2 * 12/2016 Hinman ............ A61M 25/0147
(Continued)

FOREIGN PATENT DOCUMENTS

JP    S63-095028 A    4/1988
JP    2009-219795 A   10/2009
(Continued)

*Primary Examiner* — Lynsey C Eiseman
*Assistant Examiner* — Rumaisa Rashid Baig
(74) *Attorney, Agent, or Firm* — Oliff PLC

(57) ABSTRACT

A bending mechanism includes: a shaft part; a bendable part linked to the shaft part; a forward end part linked to the bendable part; an operating rod or an operating wire inserted through grooves or holes of the shaft part and the bendable part and having a distal end thereof fixed to the bendable part; and a pressing portion configured to be able to press the operating rod or the operating wire against a fixed portion of the shaft part. The bendable part is configured to be bendable as a result of the operating rod or the operating wire being operated in an extending direction thereof. The operating rod or the operating wire is configured such that, when pressed against the fixed portion of the shaft part by the pressing portion, the operating rod or the operating wire is fixed by friction force.

10 Claims, 12 Drawing Sheets

(58) Field of Classification Search
CPC ............... A61B 1/0055; A61B 1/0057; A61B
2017/00535; A61B 2017/2946; A61B
17/29; A61B 17/3417; A61B 17/00234;
A61B 17/3421; A61B 17/3423; A61B
34/70; A61B 2017/00318; A61B
2017/00991; A61B 2017/2901; A61B
2017/2906; A61B 2017/2927; A61B
2017/3443; A61B 2090/508; F16C
2316/10; F16C 1/04
See application file for complete search history.

(56) References Cited

U.S. PATENT DOCUMENTS

| | | | | |
|---|---|---|---|---|
| 10,016,213 B2* | 7/2018 | Kobayashi | | A61B 17/3417 |
| 2004/0236316 A1* | 11/2004 | Danitz | | A61B 34/70 |
| | | | | 606/1 |
| 2005/0054899 A1* | 3/2005 | Miyake | | A61B 1/0052 |
| | | | | 600/152 |
| 2006/0059946 A1* | 3/2006 | Watanabe | | F25B 9/002 |
| | | | | 62/515 |
| 2011/0237888 A1* | 9/2011 | Matsushita | | A61B 1/01 |
| | | | | 600/114 |
| 2012/0041266 A1* | 2/2012 | Buehs | | A61B 1/0057 |
| | | | | 600/142 |
| 2013/0085336 A1* | 4/2013 | Kasai | | A61B 1/0053 |
| | | | | 600/149 |
| 2014/0066716 A1* | 3/2014 | Arai | | A61B 1/0057 |
| | | | | 600/149 |
| 2014/0243592 A1* | 8/2014 | Kato | | A61B 17/00234 |
| | | | | 600/141 |
| 2015/0351610 A1* | 12/2015 | Fan | | A61B 1/0052 |
| | | | | 600/148 |
| 2016/0081714 A1* | 3/2016 | Kobayashi | | A61B 17/00234 |
| | | | | 606/1 |
| 2018/0206904 A1* | 7/2018 | Felder | | A61B 46/10 |
| 2019/0313884 A1* | 10/2019 | Isobe | | A61B 1/008 |

FOREIGN PATENT DOCUMENTS

| | | |
|---|---|---|
| JP | 2010-259478 A | 11/2010 |
| JP | 2015-213541 A | 12/2015 |
| JP | 2016-054967 A | 4/2016 |
| JP | 2016-509882 A | 4/2016 |
| JP | 2018-110745 A | 7/2018 |

* cited by examiner

BENDING MECHANISM AND MEDICAL EQUIPMENT

TECHNICAL FIELD

The present invention relates to a bending mechanism and medical equipment.

BACKGROUND ART

In the past, intraperitoneal surgeries, such as cholecystectomy, were performed by celiotomy, i.e., by incising the abdomen. In recent years, a laparoscopic surgery has been widely performed, in which a plurality of several-centimeter holes are made in the abdomen, and a surgical tool or the like for use in the surgery (hereinafter, simply referred to as "surgical tool or the like") and a laparoscope are inserted in the abdomen through the holes to perform a surgical procedure in the abdomen.

There are cases where the surgical tool or the like includes a bending mechanism for changing the orientation of the forward end of an insertion portion of the surgical tool or the like. Driving force for driving the bending mechanism is transmitted by a wire or a rod from the base end side of the surgical tool or the like to the bending mechanism.

The above bending mechanism has bending stiffness that is dependent on the cross-sectional shape and mechanical properties of the wire or the rod. In some cases, the bending mechanism is required to have high bending stiffness due to the type of the surgery to be performed. Conventionally, a bending mechanism having high stiffness has been proposed (see Patent Literature 1, for example). In the proposed bending mechanism, one wire guide hole positioned at a joint ring, and another wire guide hole positioned adjacently to and in series with the one wire guide hole, are different from each other in terms of the direction or position of their axis. An operating wire intended for shape retention (hereinafter, "shape-retention operating wire") is inserted through these wire guide holes. Tensile force is applied to the shape-retention operating wire, and in accordance with increase in the tensile force, frictional resistance applied to portions of the shape-retention operating wire, the portions being in contact with the wire guide holes, increases. Consequently, in a state where such shape-retention operating wires are not pulled from the base end side, a bent-shape-retainable tubular part is easily deformed, i.e., the stiffness of the bending mechanism is reduced, whereas in a state where such shape-retention operating wires are pulled from the base end side, the bent-shape-retainable tubular part is not easily deformed, i.e., the stiffness of the bending mechanism is increased.

CITATION LIST

Patent Literature

PTL 1: Japanese Laid-Open Patent Application Publication No. 2010-259478

SUMMARY OF INVENTION

Technical Problem

However, in the above-described conventional art of Patent Literature 1, the bendable part is required to have a space for the shape-retention operating wires and the wire guide holes, and also, the guide holes are required to have complex shapes. Further, in the conventional art, it is necessary to have sliding durability between the shape-retention operating wires and the guide holes.

The present invention has been made in order to solve the above-described problems. An object of the present invention is to increase the stiffness of the bending mechanism with a simple configuration.

Solution to Problem

A bending mechanism according to one aspect of the present invention includes: a shaft part; a bendable part whose proximal end is linked to a distal end of the shaft part, the bendable part being bendable in a direction orthogonal to an axis of the shaft part; a forward end part whose proximal end is linked to the bendable part; an operating rod, or an operating wire, inserted through a groove or a hole of the shaft part and a groove or a hole of the bendable part, the groove or the hole of the shaft part being provided in a manner to extend along an axial direction of the shaft part, the groove or the hole of the bendable part being provided in a manner to extend along an axial direction of the bendable part, the operating rod or the operating wire having a distal end thereof fixed to the bendable part; and a pressing portion configured to be able to press the operating rod or the operating wire against a fixed portion of the shaft part. The bendable part is configured to be bendable as a result of the operating rod or the operating wire being operated in an extending direction of the operating rod or the operating wire. The operating rod or the operating wire is configured such that, when the operating rod or the operating wire is pressed against the fixed portion of the shaft part by the pressing portion, friction force is generated, and at a pressing position where the operating rod or the operating wire is pressed against the fixed portion of the shaft part, the operating rod or the operating wire is fixed in the axial direction by the friction force.

According to the above configuration, the operating rod or the operating wire, which is inserted through the groove or the hole of the shaft part and the groove or the hole of the bendable part, the groove or the hole of each part being provided in a manner to extend along the axial direction, is operated in the extending direction of the operating rod or the operating wire, thereby bending the bendable part. The pressing portion presses the operating rod or the operating wire against the fixed portion of the shaft part (e.g., a wall surface of the groove or the hole of the shaft part). As a result, friction force is generated, and at the pressing position, the operating rod or the operating wire is fixed in the axial direction by the friction force. This makes it possible to increase the stiffness of the bending mechanism with a simple configuration.

The bendable part may include: a first bendable part bendable in a first direction orthogonal to the axial direction of the shaft part; and a second bendable part bendable in a second direction orthogonal to the axial direction of the shaft part, the second direction being different from the first direction.

According to the above configuration, the bending direction of the first bendable part and the bending direction of the second bendable part are different from each other. This makes it possible to allow the bending mechanism to rotate (bend) more freely in various directions.

The pressing portion may include a tube that is inserted through the groove or the hole of the shaft part adjacently to the operating rod or the operating wire, the tube being expandable by being supplied with fluid pressure. The tube may be configured to expand by being supplied with the fluid pressure and be able to press the operating rod or the operating wire against the fixed portion of the shaft part.

According to the above configuration, the tube expandable by the fluid pressure is expanded, and thereby the operating rod or the operating wire is pressed against the fixed portion of the shaft part (e.g., the wall surface of the groove or the hole of the shaft part). In this manner, friction force can be generated. The tube is merely required to be inserted through the groove or the hole of the shaft part together with the operating rod or the operating wire. This makes it possible to increase the stiffness of the bending mechanism with a simple configuration. A plurality of the operating rods or a plurality of the operating wires may be arranged around the tube.

The pressing portion may further include a spacer rod inserted through the groove or the hole of the shaft part in the axial direction, the spacer rod disposed in a gap that is formed between the tube and at least one of the fixed portion of the shaft part and the operating rod or the operating wire.

According to the above configuration, since the spacer rod is inserted through the groove or the hole of the shaft part such that the spacer rod is disposed at a position around the tube, the space for the tube is reduced. Consequently, even if the fluid pressure supplied to the tube at the time of expanding the tube is reduced, sufficient friction force is generated, and thereby the pressing effect can be obtained. In addition, since the fluid pressure supplied to the tube can be reduced, the tube is less likely to excessively stretch and tear, which makes it possible to improve the pressure-withstanding performance of the tube.

A cross section of the groove or the hole of the shaft part, the cross section being perpendicular to the axial direction, may have a predetermined shape. A cross section of the tube may have a shape that at least partly corresponds to the predetermined shape of the cross section of the groove or the hole. Specifically, the cross section of the groove or the hole of the shaft part, the cross section being perpendicular to the axial direction, may have a rectangular shape. An outer shape of the cross section of the tube may be rectangular corresponding to the shape of the cross section of the groove or the hole. An inner shape of the cross section of the tube may be circular.

The bendable part may include a plurality of segment members that are linked together to form one line in the axial direction of the bendable part. The operating rod or the operating wire may be inserted through grooves or holes of the plurality of segment members, the grooves or the holes being provided over the plurality of segment members in a manner to extend in the axial direction. The distal end of the operating rod or the operating wire may be fixed to the segment member that is positioned at a distal end of the bendable part.

According to the above configuration, the bendable part is constituted mainly by the segment members. This makes it possible to simplify the configuration of the bending mechanism.

The above bending mechanism may further include a restraining rod, or a restraining wire, inserted through the grooves or the holes of the plurality of segment members, the grooves or the holes being provided over the plurality of segment members in a manner to extend in the axial direction, the restraining rod or the restraining wire having a distal end thereof fixed to the segment member that is positioned closer to the proximal end of the bendable part than the segment member that is positioned at the distal end of the bendable part. The restraining rod or the restraining wire may be configured to be pressed against the fixed portion of the shaft part by the pressing portion.

According to the above configuration, in a deflection mode in which, when external force is applied to the forward end of the bendable part, the forward end of the bendable part is deflected in the direction of the external force regardless of the amount of elongation of the operating rod or the operating wire, the deflection of the forward end of the bendable part can be restrained.

The fixed portion of the shaft part may be a wall surface of the groove or the hole of the shaft part.

According to the above configuration, the wall surface of the groove or the hole of the shaft part can be used as the fixed portion of the shaft part. This makes it possible to simplify the configuration of the bending mechanism.

Medical equipment according to another aspect of the present invention includes the above-described bending mechanism.

Advantageous Effects of Invention

The present invention makes it possible to increase the stiffness of the bending mechanism with a simple configuration.

DESCRIPTION OF EMBODIMENTS

Figure 1:
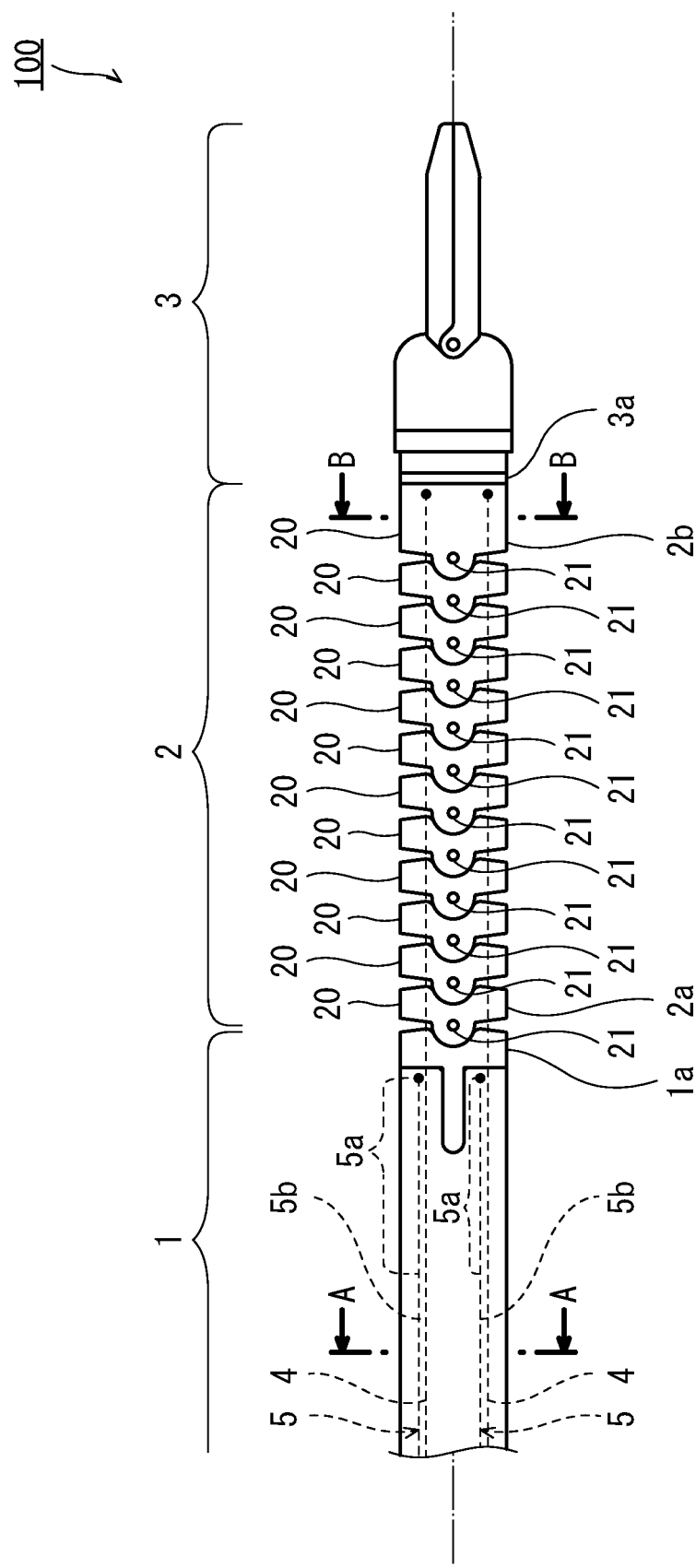
FIG. 1 is a side view showing one example of a bending mechanism according to Embodiment 1 of the present invention.

Hereinafter, embodiments of the present invention are described with reference to the drawings. In the drawings, the same or corresponding elements are denoted by the same reference signs, and repeating the same descriptions is avoided below.

Embodiment 1

FIG. 1 is a side view showing one example of a bending mechanism according to Embodiment 1 of the present invention. As shown in FIG. 1, a bending mechanism 100 includes: a hollow shaft part 1; a hollow bendable part 2 whose proximal end 2a is linked to a distal end 1a of the shaft part 1; a forward end part 3 whose proximal end 3a is linked to a distal end 2b of the bendable part 2; operating rods 4 inserted through the shaft part 1 and the bendable part 2 in axial directions of the shaft part 1 and the bendable part 2, the operating rods 4 having their distal ends fixed to the distal portion of the bendable part 2; and pressing portions 5 configured to be able to press the respective operating rods 4 against the shaft part 1. It should be noted that the term "linked" herein means not only a case where two things are directly connected to each other, but also a case where another thing is interposed between the two things, i.e., the two things are connected to each other indirectly. In the description below, the term "axis" means a center line of the bending mechanism 100, the center line extending from the forward portion to the backward portion of the bending mechanism 100, and the term "axial direction" means a direction along the axis (i.e., the forward-backward direction). In the present embodiment, the shaft part 1, the bendable part 2, and the forward end part 3 are linked together such that the axial directions of these respective parts coincide with the axial direction of the bending mechanism 100.

Figure 2:
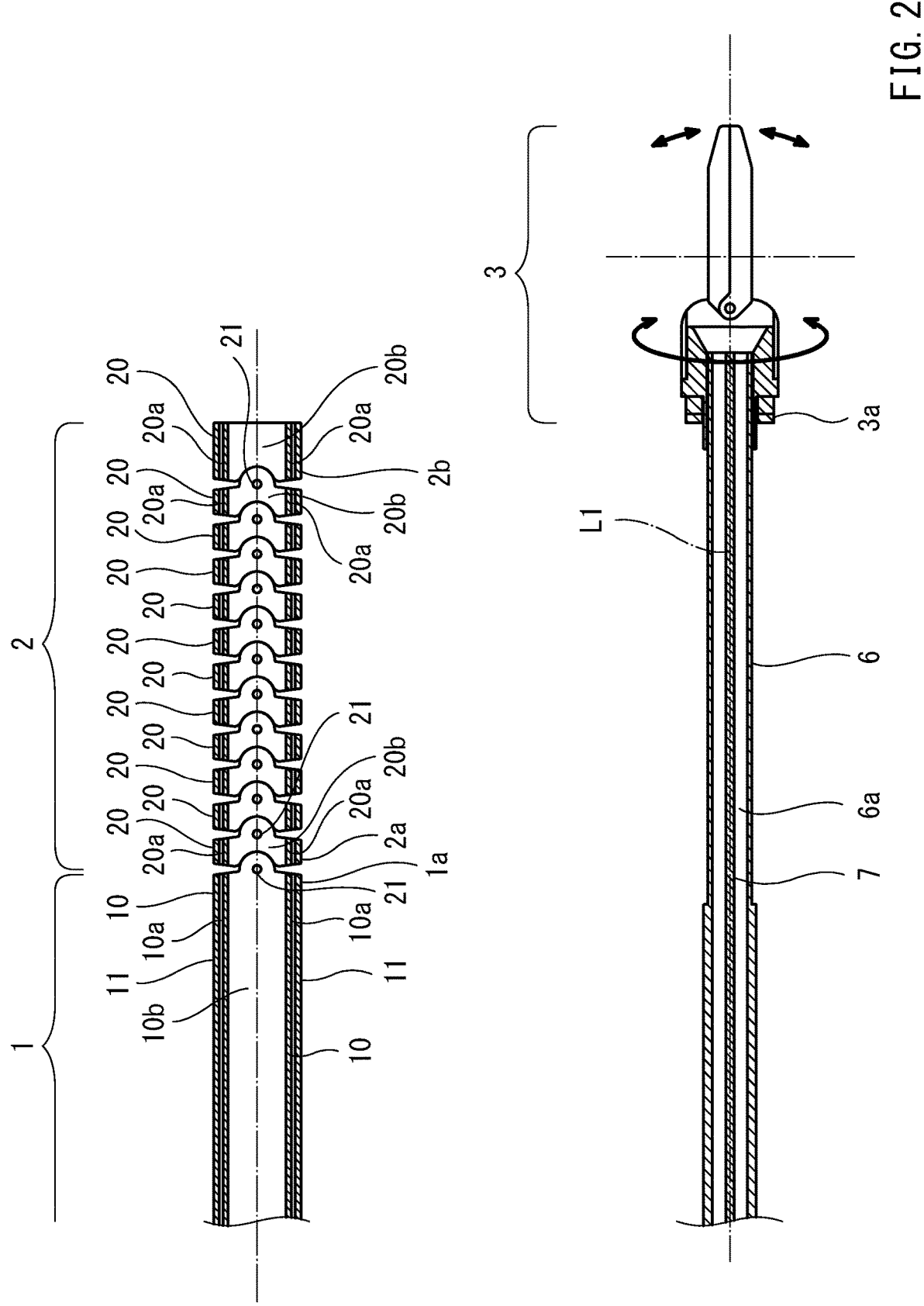
FIG. 2 shows sectional views of respective parts of the bending mechanism of FIG. 1, the sectional views each being taken along the axial direction of the bending mechanism.

FIG. 2 shows sectional views of these respective parts, the sectional views each being taken along the axial direction of the bending mechanism 100. As shown in FIG. 2, the shaft part 1 includes a shaft 10 and an outer tube 11. The shaft 10 is a tubular member. The outer tube 11 covers the outer periphery of the shaft 10. The shaft 10 is provided with grooves 10a, which allow the operating rods 4 and the pressing portions 5 (see FIG. 1) to be inserted therethrough. The grooves 10a are provided on the outer surface of the shaft 10 in a manner to extend along the axial direction of the shaft 10. The shaft 10 is further provided with an interior space 10b, which allows a hollow inner tube 6 to be inserted therethrough. The interior space 10b is provided in a manner to extend along the axial direction of the shaft 10.

The bendable part 2 includes a plurality of segment members 20, which are linked together to form one line in the axial direction of the bendable part 2. In the present embodiment, twelve segment members 20 are linked together to form one line in the axial direction of the bendable part 2. Each of the plurality of segment members 20 includes through-holes 20a and an interior space 20b. The through-holes 20a are provided in a manner to extend in the axial direction of the bendable part 2, and allow the operating rods 4 to be inserted therethrough. The interior space 20b is provided in a manner to extend in the axial direction of the bendable part 2, and allows the hollow inner tube 6 to be inserted therethrough. Each pair of adjacent segment members 20 is coupled together by a pair of pins 21. The distal end 1a of the shaft part 1 is coupled, by a pair of pins 21, to the segment member 20 positioned at the proximal end 2a of the bendable part 2. In this manner, each segment member 20 is coupled to its adjacent segment member 20, such that each segment member 20 is swingable about the axis of the pair of pins 21 (i.e., swingable about a swing axis). The swing axes of the respective segment members 20 are configured to be parallel to each other. That is, the bendable part 2 is configured to be bendable in respective directions orthogonal to the axes and the swing axes of the segment members 20.

The forward end part 3 is an end effector, and the end effector of the present embodiment serves as medical forceps. The forward end part 3 includes a base 30, which is mounted to the distal end of the inner tube 6, which is inserted through the inside of the shaft part 1 and the bendable part 2. The base 30 is rotatable about a rotational axis L1, which passes through the center of the inner tube 6 (i.e., rotatable about a wrist rotational axis). The inner tube 6 of the present embodiment is a metal tube made of a stainless steel tape wound in a spiral manner. The inner tube 6 allows bending thereof and is capable of transmitting a torque. The inner tube 6 also includes an interior space 6a, in which wires can be accommodated. The inner tube 6 is inserted through the interior space 10b of the shaft 10 and the interior spaces 20b of the plurality of segment members 20.

In the present embodiment, a rod 7, which drives the forceps, is inserted through the interior space 6a of the inner tube 6. The distal end of the rod 7 is coupled to a mechanism (not shown) that drives the forceps to open and close. The mechanism is configured to, when a portion thereof coupled to the distal end of the rod 7 is moved in a predetermined direction, cause the forceps to open or close by a predetermined amount corresponding to the moving amount of the portion coupled to the distal end of the rod 7. Accordingly, for example, when the rod 7 is pulled in a direction from its distal end toward its proximal end, the forceps close and grip an object. On the other hand, when the rod 7 is fed in a direction from its proximal end toward its distal end, the forceps open and release the object.

The operating rods 4 (see FIG. 1) are inserted through the grooves 10a (see FIG. 2) provided on the shaft 10 and the through-holes 20a (see FIG. 2) provided over the plurality of segment members 20. The distal ends of the respective operating rods 4 are fixed to the segment member 20 positioned at the distal end 2b of the bendable part 2, i.e., fixed to the distal portion of the bendable part 2. The distal portion of the bendable part 2, to which the distal ends of the operating rods 4 are fixed, may be disposed at any position, so long as the bendable part 2 can be driven by the operating rods 4. In the present embodiment, each operating rod 4 has a rod shape and is made of a super elastic alloy such as nickel-titanium alloy. Each operating rod 4 may be a flexible wire made of stainless steel, or may be a super elastic wire. Each operating rod 4 is configured to be movable in the extending direction of the operating rod 4 by being pushed or pulled on its base end side. Consequently, the bendable part 2 is configured to be bendable in the respective directions orthogonal to the axes and the swing axes of the segment members 20.

The pressing portions 5 (see FIG. 1) are inserted through the grooves 10a (see FIG. 2) of the shaft part 1 adjacently to the respective operating rods 4. Each pressing portion 5 includes a tube 5a and a pipe 5b. The tube 5a is made of a rubber, a thermoplastic elastomer, a resin, a metal, or a super elastic material. The pipe 5b is a hollow stainless steel pipe linked to the tube 5a. The distal ends of the respective tubes 5a are fixed at the distal ends of the respective grooves 10a of the shaft part 1, and the proximal ends of the respective tubes 5a are connected to the distal ends of the respective pipes 5b. Hydraulic pressure is supplied to the tubes 5a from the proximal end (base end) side of the pipes 5b. Each of the pipes 5*b* and a corresponding one of the tubes 5*a* are connected to each other in the following manner: covering the outer periphery of the distal portion of each pipe 5*b* with the proximal portion of the corresponding tube 5*a*; then further covering the proximal portion around with a shrinkable member; and causing the shrinkable member to shrink. For example, a thermally shrinkable resin, a thermally shrinkable elastomer, or a shape-memory alloy can be used as the shrinkable member.

Figure 3A:
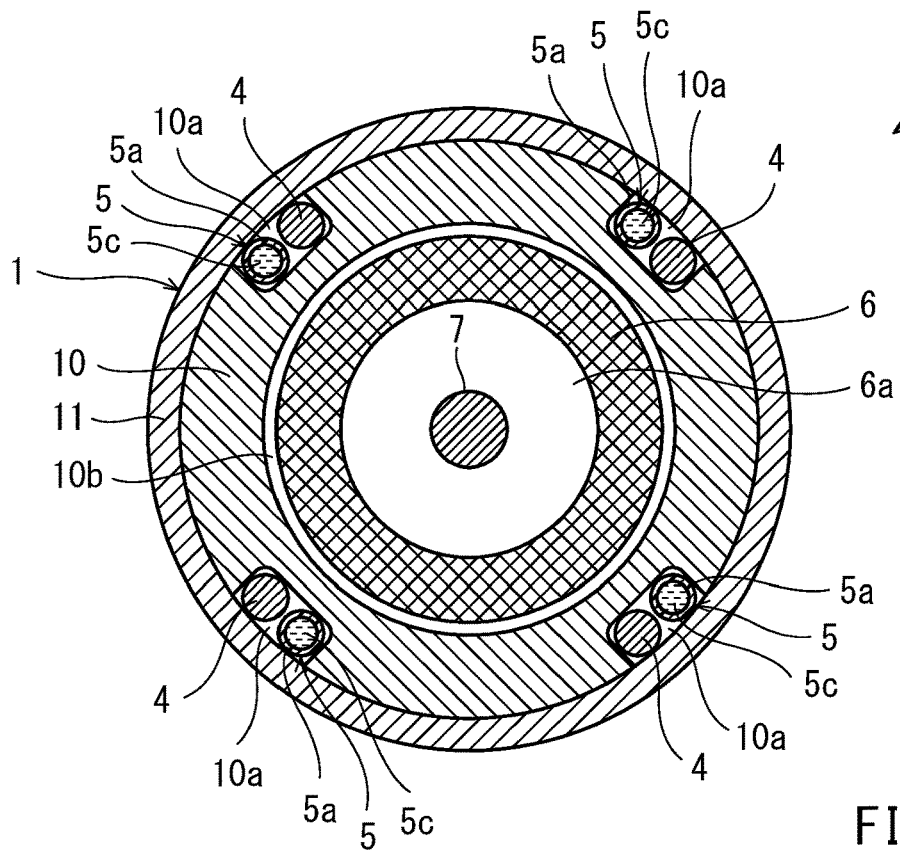
FIG. 3A is a sectional view of the bending mechanism of FIG. 1, the sectional view being taken along line A-A of FIG. 1.

FIG. 3A is a sectional view of the shaft part 1 of the bending mechanism 100 of FIG. 1, the sectional view being taken along line A-A of FIG. 1. As shown in FIG. 3A, the outer surface of the shaft 10 is provided with four grooves 10*a*. The outer surface of the shaft 10 may be provided with an arbitrary number of grooves 10*a*, which is at least one groove 10*a*. One operating rod 4 and one tube 5*a* adjacent thereto are inserted through each groove 10*a*. The outer periphery of the shaft 10 is covered with the outer tube 11. The inside of the tube 5*a* is filled with a hydraulic liquid 5*c*. The tube 5*a* is configured to be supplied with liquid pressure and to be shrinkable and expandable in accordance with a change in the pressure of the hydraulic liquid 5*c* inside the tube 5*a*. In the present embodiment, the tube 5*a* is configured to expand by being supplied with the liquid pressure from the base end (the proximal end of the pipe 5*b* of FIG. 1) side, and be able to press the operating rod 4 against the wall surface of the groove 10*a* of the shaft part 1. It should be noted that the material of the surface of the tube 5*a*, the surface coming into contact with the operating rod 4, may be a rubber or plastic.

The inner tube 6 is inserted through the interior space 10*b* of the shaft 10. The rod 7, which drives the end effector, i.e., the forward end part 3 (see FIG. 2), is inserted through the interior space 6*a* of the inner tube 6. The distal end of the rod 7 is mounted to the forceps, i.e., the forward end part 3 (the end effector).

Figure 3B:
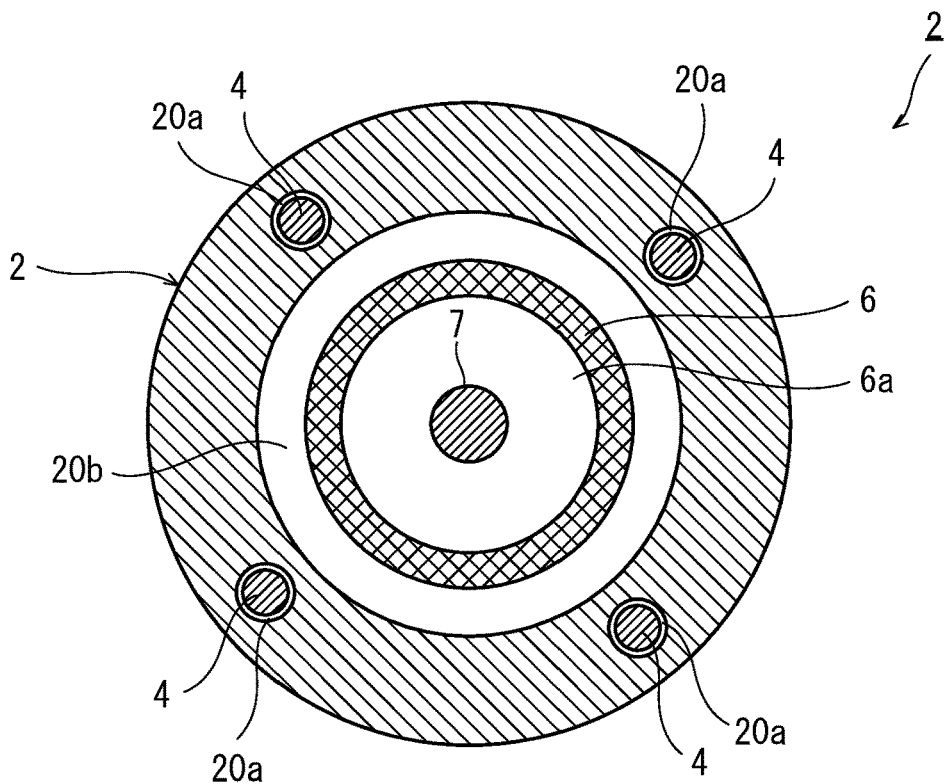
FIG. 3B is a sectional view of the bending mechanism of FIG. 1, the sectional view being taken along line B-B of FIG. 1.

FIG. 3B is a sectional view of the bendable part 2 of the bending mechanism 100 of FIG. 1, the sectional view being taken along line B-B of FIG. 1. As shown in FIG. 3B, each segment member 20 is provided with four through-holes 20*a*. The four through-holes 20*a* are formed at positions corresponding to the respective grooves 10*a* of the shaft 10. One operating rod 4 is inserted through each through-hole 20*a*. The inner tube 6 is inserted through the interior space 20*b* of the bendable part 2 (each segment member 20). As with FIG. 3A, the rod 7, which drives the end effector, i.e., the forward end part 3 (see FIG. 2), is inserted through the interior space 6*a* of the inner tube 6.

Figure 4:
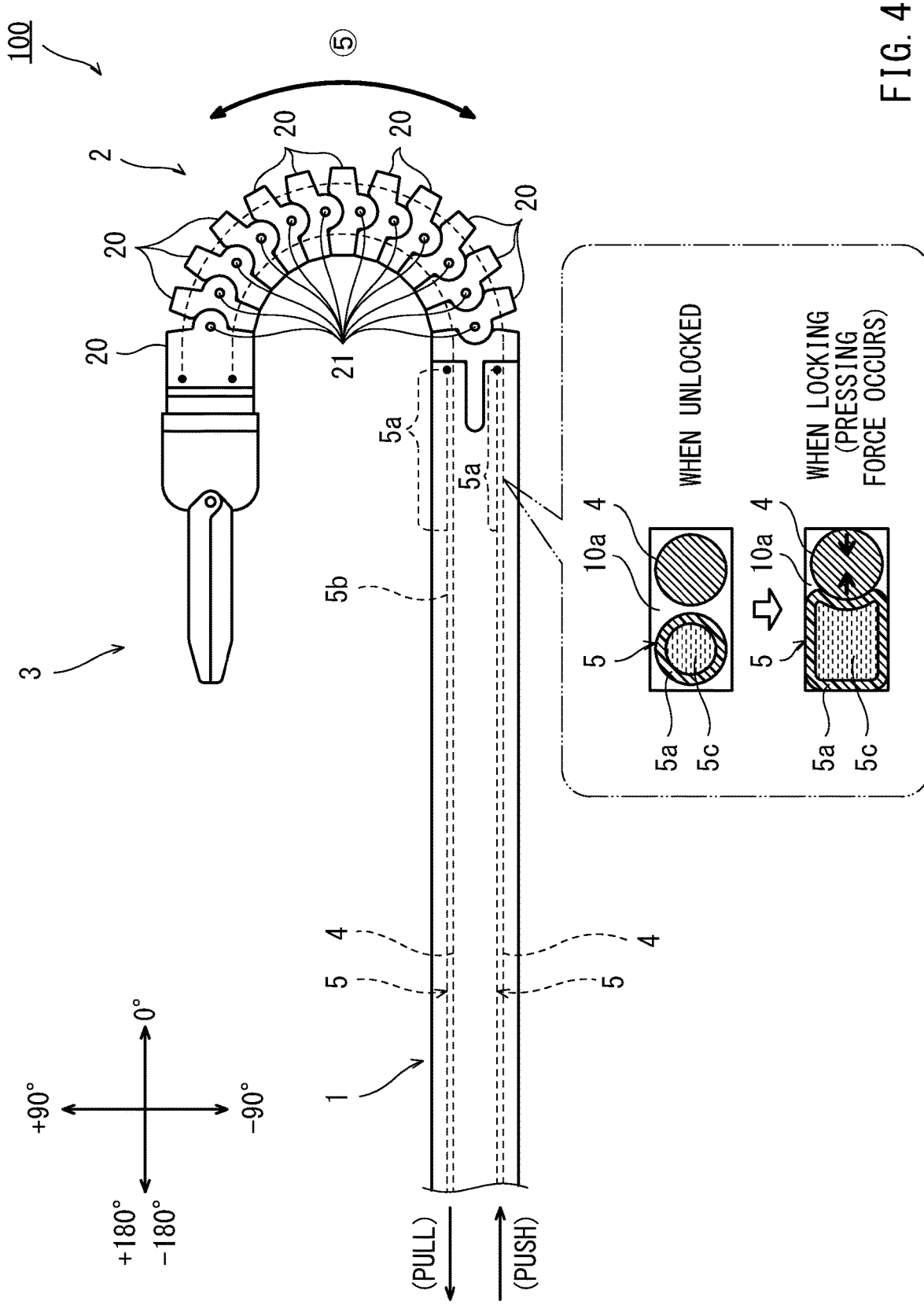
FIG. 4 illustrates a bending action and a locking action of the bending mechanism of FIG. 1.

Next, operations of the bending mechanism 100 are described with reference to FIG. 4. As shown in FIG. 4, the operating rods 4 inserted along the axial direction of the shaft part 1 and the bendable part 2 are pushed and pulled in the respective extending directions of the operating rods 4. Specifically, among the four operating rods 4 (see FIGS. 3A and 3B), two bending-side operating rods 4 (two operating rods 4 in the upper side of FIGS. 3A and 3B) are pulled to the base end side, and the two opposite-side operating rods 4 (two operating rods 4 in the lower side of FIGS. 3A and 3B) are pushed to the forward end side. Each of the plurality of segment members 20 constituting the bendable part 2 is coupled to its adjacent segment member 20, such that each segment member 20 is swingable about the axis of a pair of pins 21 (i.e., swingable about a swing axis), and the plurality of segment members 20 are configured such that the swing axes of the respective segment members 20 are parallel to each other. In the present embodiment, the bendable part 2 is bendable by ±180 degrees in a direction orthogonal to the axes and the swing axes of the segment members 20 (i.e., in the upward or downward direction in the drawing).

After such a bending action is completed, each tube 5*a* (each pressing portion 5) is expanded to press the operating rod 4 against the wall surface of the groove 10*a* provided in the shaft part 1. As a result, friction force is generated between the operating rod 4 and the wall surface of the groove 10*a*, and at the pressing position where the operating rod 4 is pressed against the wall surface of the groove 10*a*, the operating rod 4 is fixed in the axial direction. Accordingly, the length of the operating rod 4 influencing the bending stiffness of the bending mechanism 100 is the length of the operating rod 4 from its distal end to the pressing position. That is, the length of the operating rod 4 influencing the bending stiffness of the bending mechanism 100 can be shortened compared to a case where the operating rod 4 is not pressed against the wall surface of the groove 10*a* provided in the shaft part 1. Accordingly, the amount of elongation of the operating rod 4 influencing the bending stiffness of the bending mechanism 100 is reduced, and thereby the bending stiffness of the bending mechanism 100 is increased. In addition, this configuration merely requires the insertion of the operating rods 4 and the tubes 5*a* through the grooves 10*a*, which are provided along the axial direction of the shaft part 1. Thus, this configuration is simple. This makes it possible to increase the stiffness of the bending mechanism 100 with a simple configuration.

It should be noted that the force of pressing the operating rod 4 can be adjusted by the hydraulic pressure supplied to the tube 5*a* or by the length of the tube 5*a*. For example, the pressing force increases when the hydraulic pressure is increased or the length of the tube 5*a* is increased.

Hereinafter, expanding each tube 5*a* (each pressing portion 5) to press the operating rod 4 against the wall surface of the groove 10*a* provided in the shaft part 1 is referred to as "locking the bendable part 2".

The bending mechanism 100 of the present embodiment can be used in medical equipment 200. For example, the medical equipment 200 is a system by which a surgeon externally remote-controls a surgical instrument provided on the distal end of the bending mechanism 100 inserted in the body of a patient on a surgical table, thereby performing a minimally invasive surgery.

Figure 5:
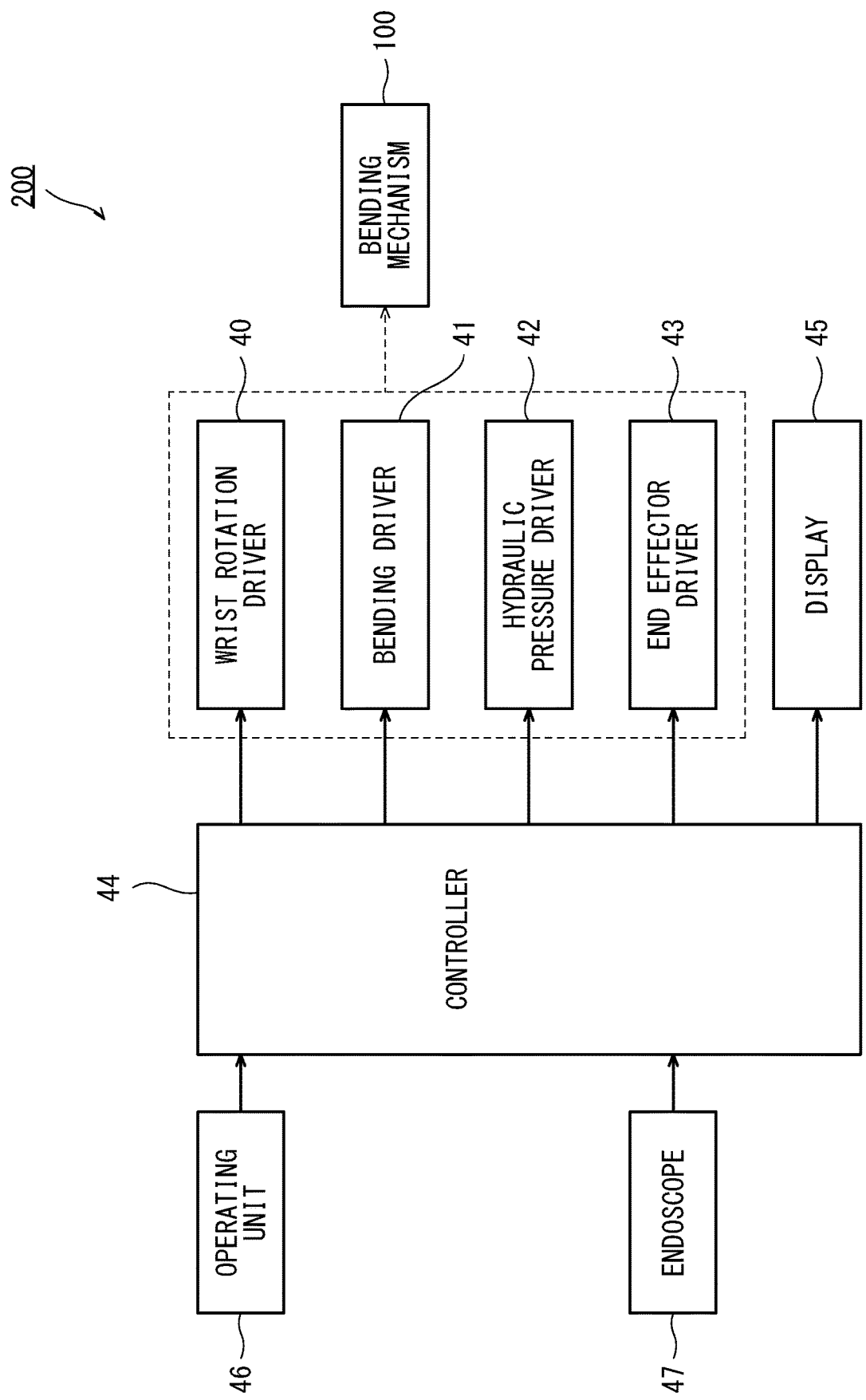
FIG. 5 is a block diagram showing a control system of medical equipment including the bending mechanism of FIG. 1.

FIG. 5 is a block diagram showing a control system of the medical equipment 200 including the bending mechanism 100. As shown in FIG. 5, the medical equipment 200 includes a wrist rotation driver 40, a bending driver 41, a hydraulic pressure driver 42, an end effector driver 43, a controller 44, a display 45, an operating unit 46, and an endoscope 47.

The wrist rotation driver 40 causes the inner tube 6, the distal end of which is mounted with the forward end part 3 (the end effector), to rotate about the rotational axis L1, thereby wrist-rotating the forceps. For example, the wrist rotation driver 40 includes a servomotor.

The bending driver 41 is connected to the operating rods 4, and causes the operating rods 4 to move (in a reciprocating manner) in the respective extending directions of the operating rods 4, thereby bending the bendable part 2. For example, the bending driver 41 includes a servomotor or servomotors.

The hydraulic pressure driver 42 is connected to the pipes 5*b* linked to the tubes 5*a*, and supplies liquid pressure from the base end side of the pipes 5*b*, thereby locking the bendable part 2.

The end effector driver 43 is connected to the rod 7, and exerts driving force causing the rod 7 to move (in a reciprocating manner) in the extending direction of the rod 7. As a result, the forceps, i.e., the end effector, open or close.

The controller 44 includes, for example, an arithmetic operation device such as a CPU and memories such as a ROM and RAM. The controller 44 may be constituted by a single control device performing centralized control, or may be constituted by a plurality of control devices performing distributed control in cooperation with each other. The controller 44 controls the action of each of the drivers (40 to 43) based on data received from the operating unit 46 to control the operations of the bending mechanism 100. The controller 44 processes image data received from the endoscope 47, and transmits the processed image data to the display 45. Predetermined control programs are stored in the memories of the controller 44. The controller 44 reads out and executes these control programs, thereby controlling the operations of the bending mechanism 100.

The operating unit 46 is configured such that a surgeon operates the operating unit 46 to input an operation command to be executed by the bending mechanism 100. The operating unit 46 is configured to be able to communicate with the controller 44. The operating unit 46 converts the operation command, which is inputted by the surgeon and which is to be executed by the bending mechanism 100, into data, and transmits the data to the controller 44.

Embodiment 2

Figure 6A:
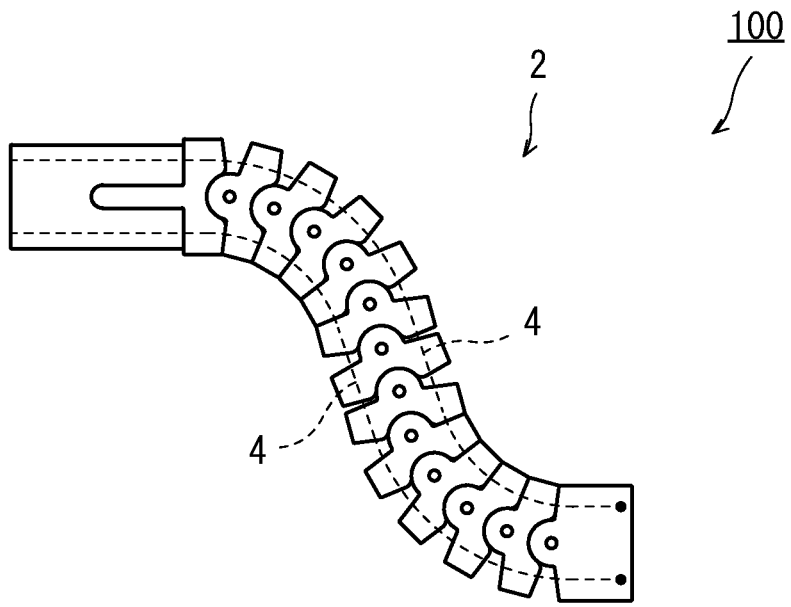
FIGS. 6A and 6B each show a deformation mode that occurs when the bending mechanism of FIG. 1 bends.
Figure 6B:
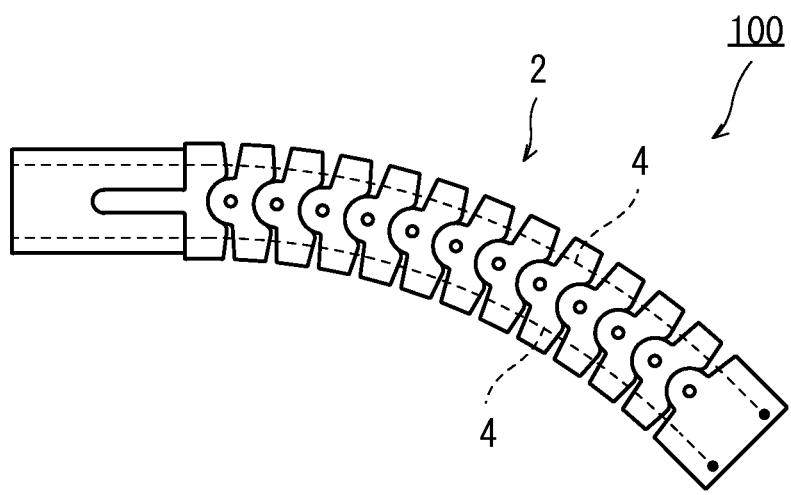

Next, a bending mechanism according to Embodiment 2 of the present invention is described with reference to the drawings. FIGS. 6A and 6B each show a deflection mode that occurs when the bendable part 2 according to Embodiment 1 bends. In a case where external force in a downward direction in FIG. 6A is applied to the forward end of the bendable part 2, the bendable part 2 shifts its shape as shown in FIG. 6A (i.e., S-shape mode). Before and after the application of the external force, the length of the operating rods 4, particularly the length of the operating rods 4 inserted through the bendable part 2, does not change. That is, the shifting of the bendable part 2 into the shape shown in FIG. 6A (i.e., into the S-shape mode) cannot be prevented by driving the operating rods 4.

Figure 7A:
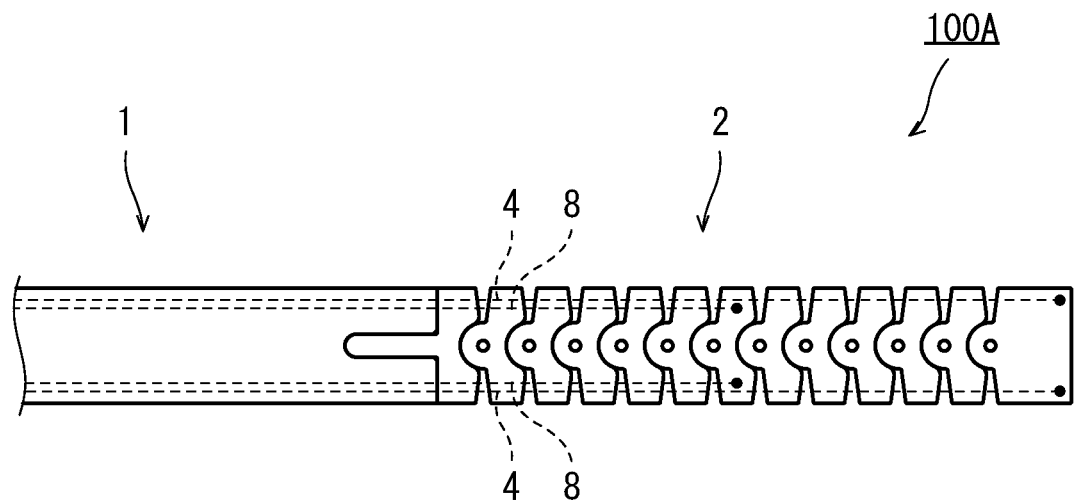
FIGS. 7A and 7B each schematically show a part of a bending mechanism according to Embodiment 2 of the present invention.

FIG. 7A schematically shows a part of a bending mechanism 100A according to Embodiment 2 of the present invention. As shown in FIG. 7A, the bending mechanism 100A according to the present embodiment is different from Embodiment 1 (see FIGS. 6A and 6B) in that the bending mechanism 100A includes restraining wires 8, which are inserted through the bendable part 2 together with the operating rods 4. In the shaft part 1, the restraining wires 8 together with the operating rods 4 are inserted through the grooves 10a, which are provided in the shaft part 1 in a manner to extend in the axial direction of the shaft part 1. In the bendable part 2, the restraining wires 8 together with the operating rods 4 are inserted through the through-holes 20a, which are provided over the plurality of segment members 20 in a manner to extend in the axial direction of the bendable part 2.

The distal ends of the restraining wires 8 are fixed to the segment member 20 that is positioned closer to the proximal end of the bendable part 2 than the segment member 20 that is positioned at the distal end of the bendable part 2. In FIG. 7A, the distal ends of the restraining wires 8 are fixed to the sixth segment member 20 counted from the proximal end of the bendable part 2. That is, the length of the restraining wires 8 in the bendable part 2 is ½ of the length of the operating rods 4 in the bendable part 2.

When each restraining wire 8 is, at the pressing position, pressed together with the operating rod 4 by the tube 5a against the wall surface of the groove 10a of the shaft part 1, the restraining wire 8 is, at the pressing position, fixed together with the operating rod 4 in the axial direction.

A deflection σ of the forward end (the right end) of the bendable part 2 in FIG. 6A, when a load in a direction perpendicular to the axial direction of the bendable part 2 is applied to the forward end of the bendable part 2, is expressed by an equation (1) shown below.

$$\sigma = (P \times L^3)/(12 \times E \times I) \quad (1)$$

In the equation (1),
P (N) is the load that is in the direction perpendicular to the axial direction of the bendable part 2 and that is applied to the forward end of the bendable part 2;
L (mm) is the length of the bendable part 2;
E (MPa) is a vertical elastic modulus; and
I (mm⁴) is a second moment of area.
($I = \pi \times d^4/64 \times N$ (Where d (mm) is the diameter of each operating rod 4, and N is the number of operating rods 4.))

When the restraining wires 8 are fixed at the respective pressing positions, the length of the restraining wires 8 from the pressing positions to the positions where the distal ends of the restraining wires 8 are fixed is kept constant. Accordingly, the S-shape mode occurs in two stages, i.e., one from the proximal portion of the bendable part 2 to the positions where the distal ends of the restraining wires 8 are fixed, and the other from the positions where the distal ends of the restraining wires 8 are fixed to the distal portion of the bendable part 2. The deflection σ of the forward end of the bendable part 2 is proportional to the cube of the length of the bendable part 2. Therefore, the deflection σ of the forward end of the bendable part 2 in a case where the S-shape mode has occurred in two stages is less than the deflection σ of the forward end of the bendable part 2 in a case where the S-shape mode has occurred in only one stage. That is, the deflection σ of the forward end of the bendable part 2 due to the S-shape mode can be restrained.

In reality, in a case where external force in a downward direction in FIG. 6B is applied to the forward end of the bendable part 2, another mode of deflection of the bendable part 2 as shown in FIG. 6B also occurs. That is, the deflection in the mode shown in FIG. 6A and the deflection in the mode shown in FIG. 6B occur concurrently. The deflection in the mode shown in FIG. 6B occurs when the upper operating rod 4s in FIG. 6B are extended and the lower operating rods 4 in FIG. 6B are retracted.

Figure 7B:
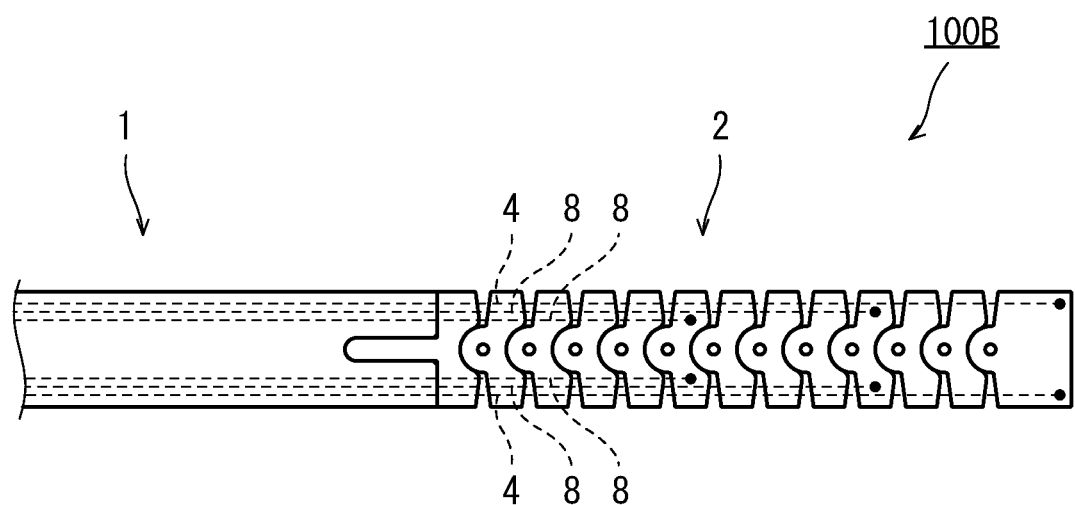

FIG. 7B schematically shows a part of another bending mechanism 100B according to Embodiment 2 of the present invention. The bending mechanism 100A of FIG. 7A includes one restraining wire 8 for each operating rod 4. On the other hand, in FIG. 7B, the bending mechanism 100B includes two restraining wires 8 for each operating rod 4.

In FIG. 7B, the distal end of one restraining wire 8 is fixed to the ninth segment member 20 counted from the proximal end of the bendable part 2, and the distal end of the other restraining wire 8 is fixed to the fifth segment member 20 counted from the proximal end of the bendable part 2. That is, the length of the one restraining wire 8 in the bendable part 2 is ¾ of the length of the operating rod 4 in the bendable part 2, and the length of the other restraining wire 8 in the bendable part 2 is 5/12 of the length of the operating rod 4 in the bendable part 2. In this manner, the length of the one restraining wire 8 in the bendable part 2 is set to be greater than ⅔ of the length of the operating rod 4 in the bendable part 2, and the length of the other restraining wire 8 in the bendable part 2 is set to be greater than ⅓ of the length of the operating rod 4 in the bendable part 2. This makes it possible to further restrain the deflection of the forward end of the bendable part 2.

In this case, for the same reasons as those described with reference to FIG. 7A, the S-shape mode occurs in three stages, which makes it possible to further restrain the deflection σ of the forward end of the bendable part 2.

Figure 8:
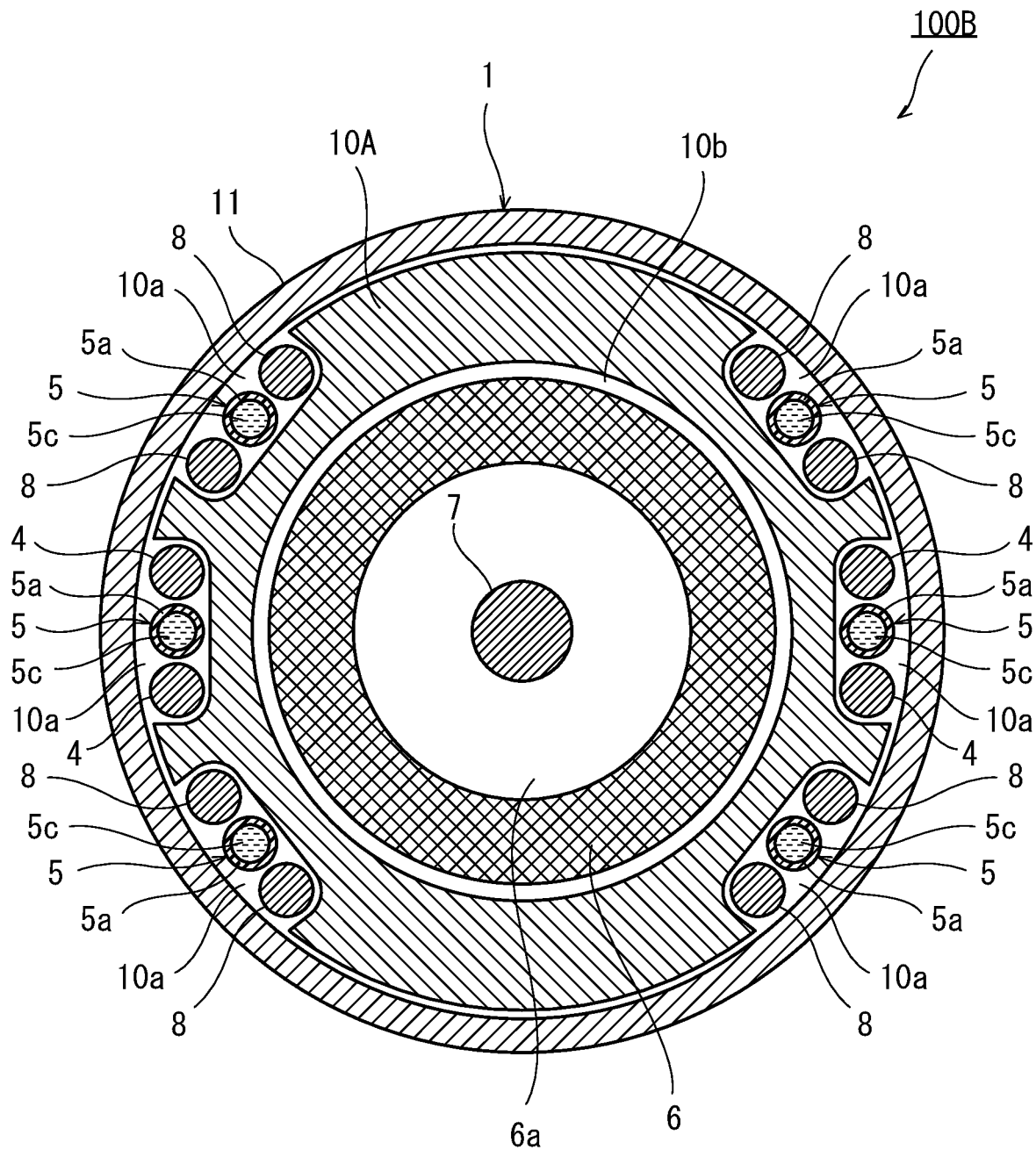
FIG. 8 shows one example of a sectional view of a shaft part of the bending mechanism of FIG. 7B.

FIG. 8 shows one example of a sectional view of the shaft part 1 of the bending mechanism 100B of FIG. 7B. As shown in FIG. 8, six grooves 10a are provided on the outer surface of a shaft 10A. The cross-sectional shape of each groove 10a is substantially rectangular. One tube 5a is inserted through each groove 10a such that, in each groove 10a, the one tube 5a is positioned between two operating rods 4 or between two restraining wires 8. In the present embodiment, four operating rods 4, eight restraining wires 8, and six tubes 5a are inserted through the grooves 10a of the shaft 10A. Accordingly, by expanding each tube 5a (each pressing portion 5), two operating rods 4 or two restraining wires 8 can be pressed against the wall surface of the groove 10a of the shaft part 1. It should be noted that the material of the surface of the tube 5a, the surface coming into contact with the operating rods 4 or the restraining wires 8, may be a rubber or plastic.

It should be noted that, in the present embodiment, in the bendable part 2, the length of each restraining wire 8 is set to ½, ¾, or 5/12 of the length of the operating rods 4. However, the length of each restraining wire 8 is not limited to these lengths, so long as each restraining wire 8 is shorter than the operating rods 4.

The restraining wires 8 may be configured to be operated by a servomotor or servomotors (e.g., the bending driver 41 in FIG. 5) in the extending directions of the restraining wires 8.

(Variations)

Figure 9A:
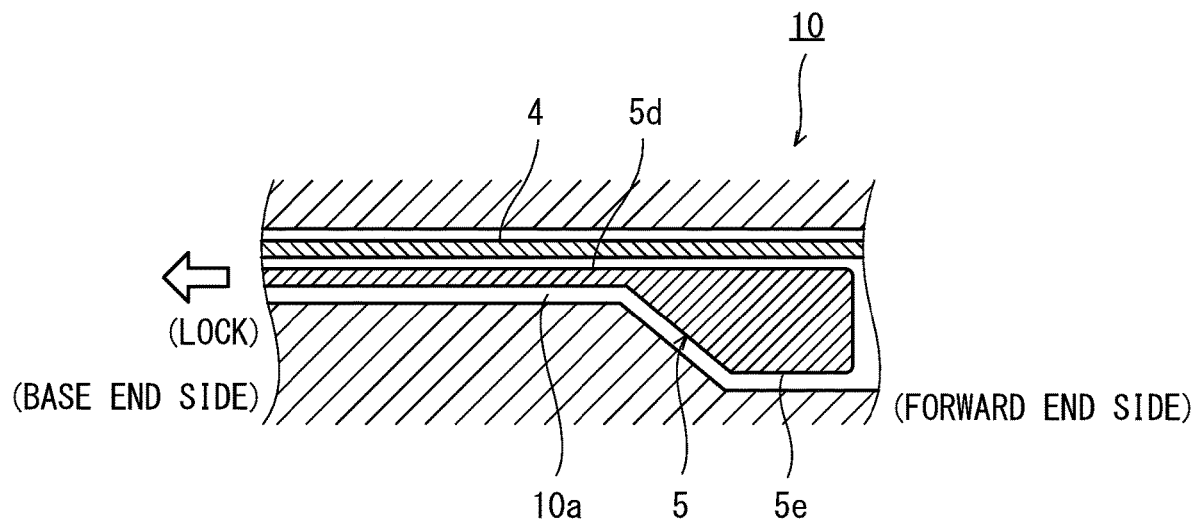
FIGS. 9A and 9B show variations of a pressing portion of the bending mechanism.
Figure 9B:
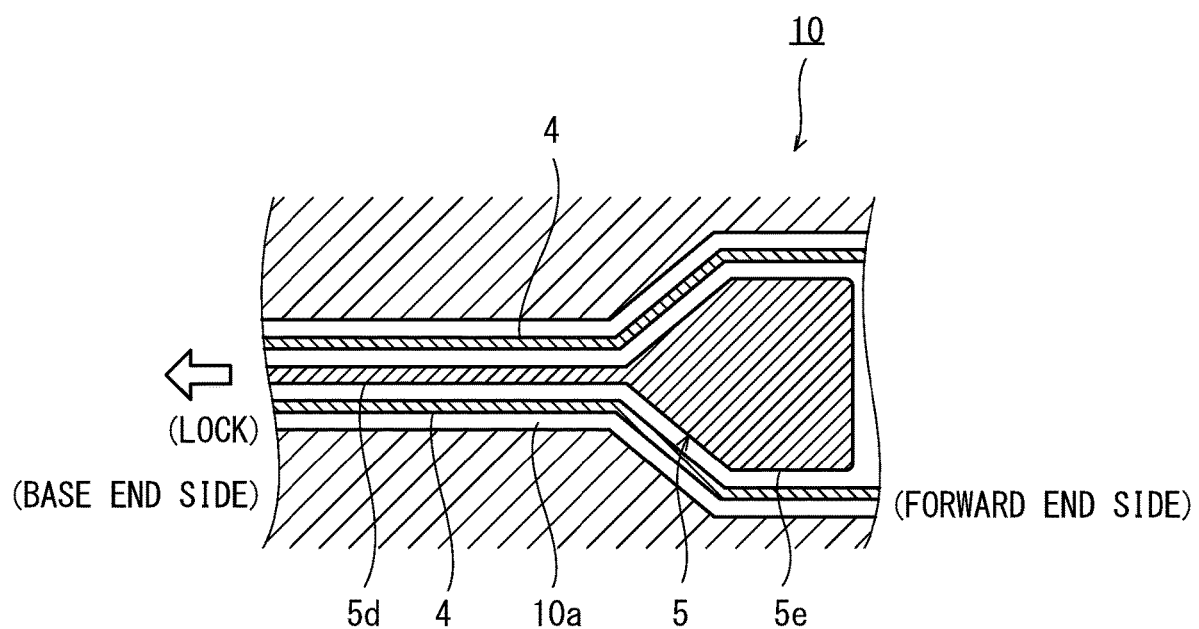

In the above-described embodiment, each pressing portion 5 includes the tube 5a, and is configured such that the tube 5a is expanded by liquid pressure to press the operating rod 4 against the shaft part 1. However, the configuration of the pressing portion 5 is not thus limited. FIGS. 9A and 9B show variations of the pressing portion 5. Each of FIGS. 9A and 9B is an enlarged plan view of a part of the outer surface of the shaft 10. As shown in FIG. 9A, the pressing portion 5 according to a first variation is inserted through the groove 10a of the shaft 10 adjacently to the operating rod 4. The pressing portion 5 includes a rod portion 5d and an enlarged portion 5e. The enlarged portion 5e is enlarged from the base end side of the shaft part 1 toward the forward end side of the shaft part 1. The rod portion 5d and the enlarged portion 5e are, for example, made of the same material as that of the operating rod 4. The groove 10a of the shaft 10 is enlarged from the base end side of the shaft part 1 toward the forward end side of the shaft part 1. Accordingly, by pulling the rod portion 5d of the pressing portion 5 in a direction toward the base end side (the direction indicated by an arrow in the drawing), the enlarged portion 5e comes into surface contact with one wall surface of the groove 10a, and the operating rod 4 adjacent to the enlarged portion 5e is pressed against the opposite wall surface of the groove 10a. That is, the pressing is performed by utilizing the wedge effect between the pressing portion 5 and the groove 10a. It should be noted that the material of the surface on one side of each of the rod portion 5d and the enlarged portion 5e, the surface coming into contact with the operating rod 4, may be a rubber or plastic.

FIG. 9B shows the pressing portion 5 according to a second variation. As shown in FIG. 9B, the pressing portion 5 according to the second variation is inserted through the groove 10a of the shaft 10 adjacently to and between two operating rods 4. By pulling the rod portion 5d of the pressing portion 5 in a direction toward the base end side (the direction indicated by an arrow in the drawing), the enlarged portion 5e comes into surface contact with the adjacent two operating rods 4, and these adjacent operating rods 4 are each pressed against the wall surfaces of the groove 10a. It should be noted that the material of the surfaces on both sides of the pressing portion 5 (the rod portion 5d and the enlarged portion 5e), the surfaces coming into contact with the respective operating rods 4, may be a rubber or plastic.

It should be noted that, in the bending mechanism 100 of the above-described embodiment (see FIG. 4), the bendable part 2 is configured to be bendable by ±180 degrees in a first direction orthogonal to the axial direction of the shaft part 1 (i.e., in the upward or downward direction in the drawing). However, the configuration of the bendable part 2 is not thus limited. The bendable part 2 may be configured to be bendable not only in the first direction, but also in a second direction that is orthogonal to the axial direction of the shaft part and that is different from the first direction.

Figure 10:
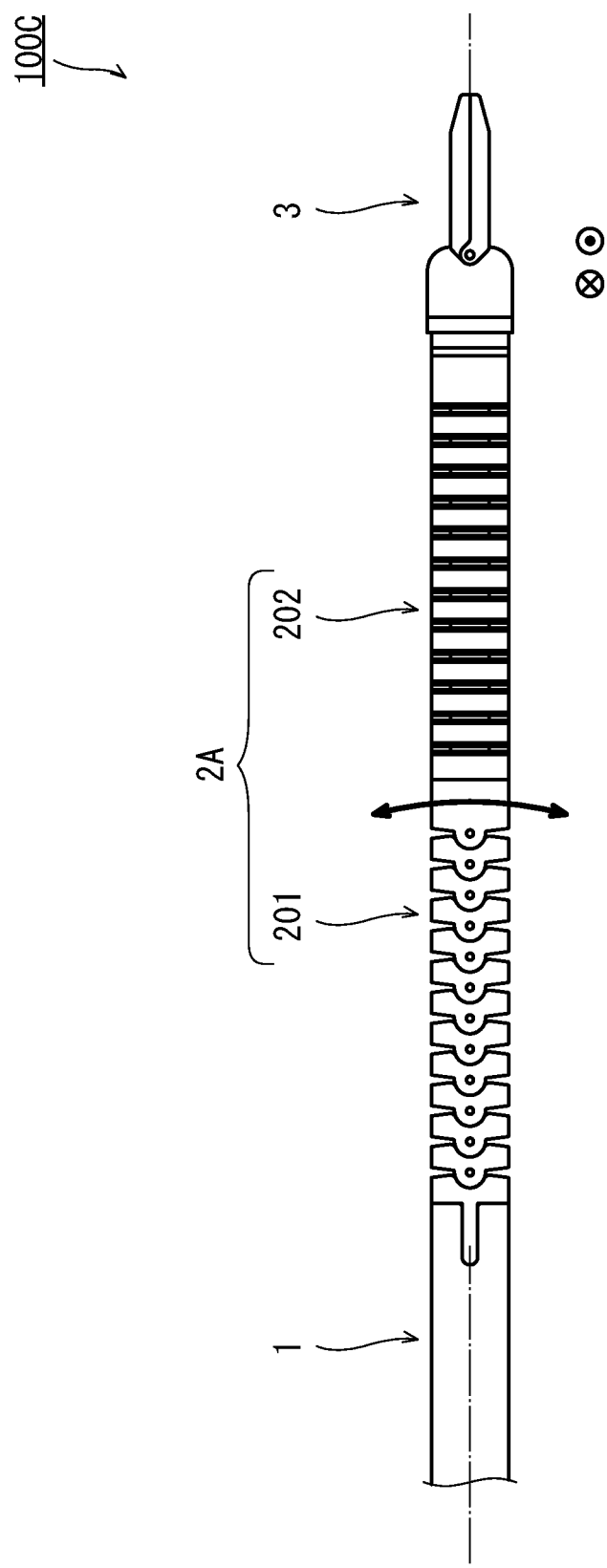
FIG. 10 is a side view showing a variation of a bendable part of the bending mechanism.

FIG. 10 is a side view showing a variation of the bendable part 2. As shown in FIG. 10, in a bending mechanism 100C, a bendable part 2A of the present variation includes a first bendable part 201 and a second bendable part 202. The proximal end of the first bendable part 201 is linked to the distal end of the shaft part 1. The proximal end of the second bendable part 202 is linked to the distal end of the first bendable part 201.

The first bendable part 201 includes a plurality of segment members that are linked together to form one line in the axial direction of the first bendable part 201. Each segment member is coupled to its adjacent segment member, such that each segment member is swingable about the axis of a pair of pins. Accordingly, the first bendable part 201 is configured to be bendable in a first direction orthogonal to the axial direction of the shaft part 1 (i.e., in the upward or downward direction in FIG. 10).

The second bendable part 202 includes a plurality of segment members that are linked together to form one line in the axial direction of the second bendable part 202. Each segment member is coupled to its adjacent segment member, such that each segment member is swingable about the axis of a pair of pins. The pin axes of the segment members of the second bendable part 202 are orthogonal to the pin axes of the segment members of the first bendable part 201. The second bendable part 202 is configured to be bendable in a second direction that is orthogonal to the axial direction of the shaft part 1 and to the first direction (i.e., bendable in a direction toward the front side or the depth side of FIG. 10). In this manner, connections are made such that the bending directions of the respective bendable parts (201 and 202) are different from each other. This makes it possible to allow the bending mechanism 100C to rotate (bend) more freely in various directions.

In addition, in the bendable part 2, the segment members may be coupled to each other in such a manner that the pin axes of the segment members are alternately orthogonal to each other.

Figure 11A:
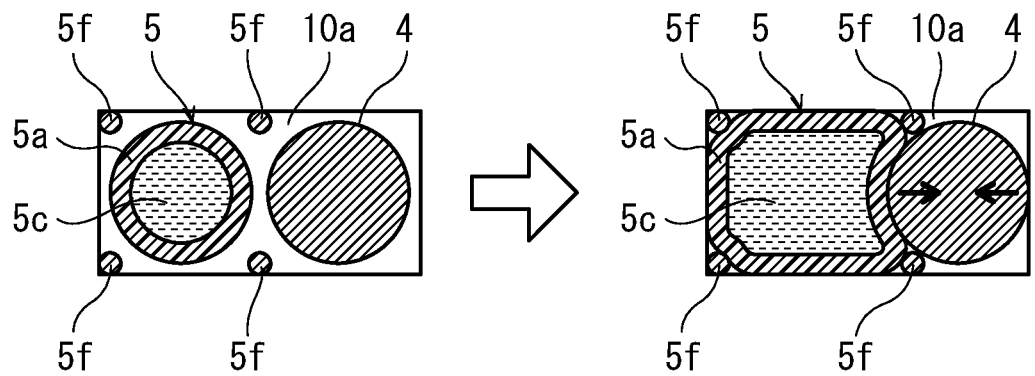
FIGS. 11A to 11C are sectional views showing other variations of the pressing portion of the bending mechanism.
Figure 11B:
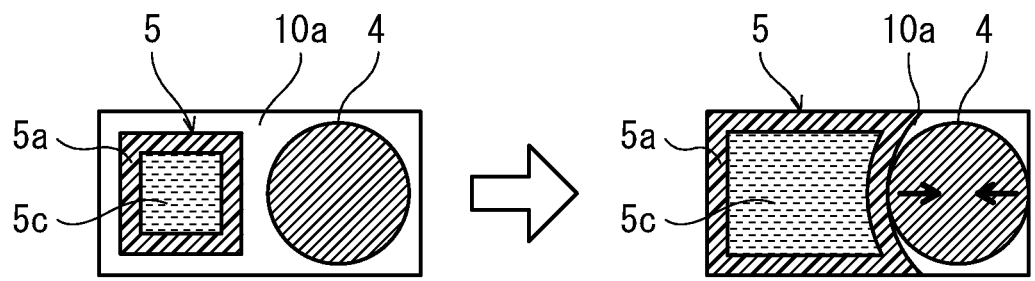
Figure 11C:
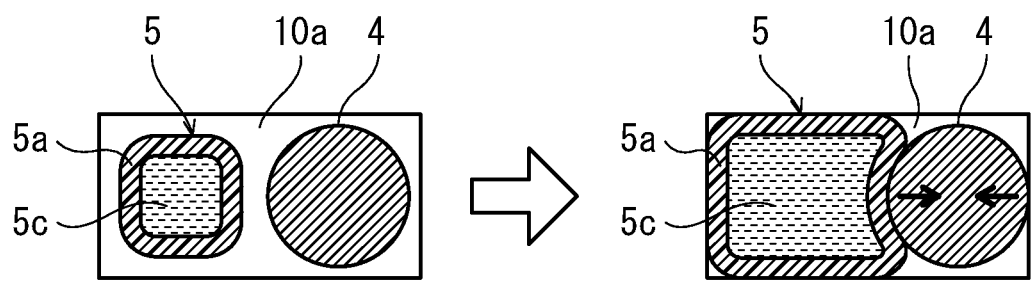

FIGS. 11A to 11C are sectional views showing other variations of the pressing portion 5 of the bending mechanism of the above embodiments. Each of these sectional views schematically shows part of a cross section of the shaft part 1 perpendicular to the axial direction of the shaft part 1. As shown in FIG. 11A, the pressing portion 5 of the present variation is different from that of Embodiment 1 (FIG. 4) in that the pressing portion 5 further includes four spacer rods 5f, which are inserted through the groove 10a of the shaft part 1 in the axial direction of the groove 10a and which are arranged around the tube 5a. The material of each spacer rod 5f is, for example, stainless steel. The material of each spacer rod 5f may be a different kind of metal, or may be a resin including plastic or a rubber. The cross-sectional shape of the groove 10a is substantially rectangular. Each of the tube 5a, the spacer rods 5f, and the operating rod 4 has a circular cross-sectional shape. The diameter of the circular cross section of the tube 5a is substantially the same as the diameter of the circular cross section of the operating rod 4. The diameter of the circular cross section of each spacer rod 5f is less than the diameter of the circular cross section of the operating rod 4.

Two of the spacer rods 5f are disposed in a gap that is formed between the tube 5a and two corners of the groove 10a. The other two spacer rods 5f are disposed in a gap that is formed between the tube 5a, the wall surface of the groove 10a, and the operating rod 4.

In the present variation, since the spacer rods 5f are inserted through the groove 10a of the shaft part 1 such that the spacer rods 5f are arranged around the tube 5a, the space for the tube 5a is reduced compared to Embodiment 1. Consequently, even if the fluid pressure supplied to the tube 5a at the time of expanding the tube 5a is reduced, sufficient friction force can be generated, and thereby the pressing effect can be obtained. In addition, since the fluid pressure supplied to the tube 5a can be reduced, the tube 5a is less likely to excessively stretch and tear, which makes it possible to improve the pressure-withstanding performance of the tube 5a. Further, in the present variation, since the spacer rods 5f occupy the aforementioned two corners of the groove 10a, no local deformation of the tube 5a occurs. Therefore, the tube 5a is less likely to tear.

It should be noted that each spacer rod 5f may be required to be disposed in a gap that is formed between the tube 5a and at least one of a fixed portion of the shaft part 1 and the operating rod 4. The term "fixed portion" herein means a portion different from a movable portion such as the operating rod 4 (i.e., a wall surface or a corner of the groove 10a). Therefore, each spacer rod 5f may be disposed in a gap between the tube 5a and the operating rod 4.

Meanwhile, the cross-sectional shape of the tube 5a may correspond to the cross-sectional shape of the groove 10a. In FIG. 11B, the cross-sectional shape of the groove 10a is substantially rectangular, whereas the cross-sectional shape of the tube 5a is substantially square. In this example, since the cross-sectional shape of the groove 10a and the cross-sectional shape of the tube 5a are partly the same, even if the fluid pressure supplied to the tube 5a is reduced at the time of expanding the tube 5a, the same advantageous effects as those of the above-described variation (shown in FIG. 11A) can be obtained. In FIG. 11C, the cross-sectional shape of the tube 5a is partly linear. Also, portions of the cross-sectional shape of the groove 10a, the portions coming into contact with the linear portions of the cross-sectional shape of the tube 5a, are linear. Thus, at least part of the cross section of the tube 5a may be required to have a shape corresponding to the shape of the groove 10a.

It should be noted that each of the left-side drawings in FIGS. 11A to 11C shows a case where there are gaps around the tube 5a when the tube 5a is in a shrunk state. When the tube 5a is in a shrunk state, the tube 5a and the wall surface of the groove 10a (the fixed portion of the shaft part 1) may be partly or entirely in contact with each other. Also, when the tube 5a is in a shrunk state, the tube 5a and the operating rod 4 may be in contact with each other. It should be noted that the material of the surface of the tube 5a, the surface coming into contact with the operating rod 4, may be a rubber or plastic.

It should be noted that the outer shape of the cross section of the tube 5a, and the inner shape of the cross section of the tube 5a, may be different from each other. For example, the outer shape of the cross section of the tube may be rectangular or substantially rectangular as shown in FIGS. 11B and 11C, whereas the inner shape of the cross section of the tube may be circular as shown in FIG. 11A.

Figure 12A:
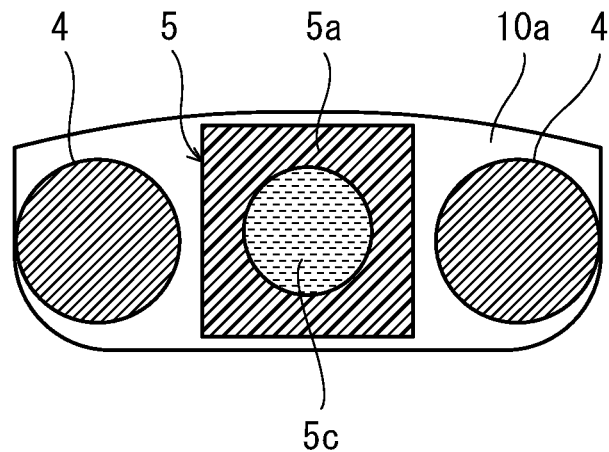
FIGS. 12A and 12B are sectional views showing yet another variation of the pressing portion of the bending mechanism.
Figure 12B:
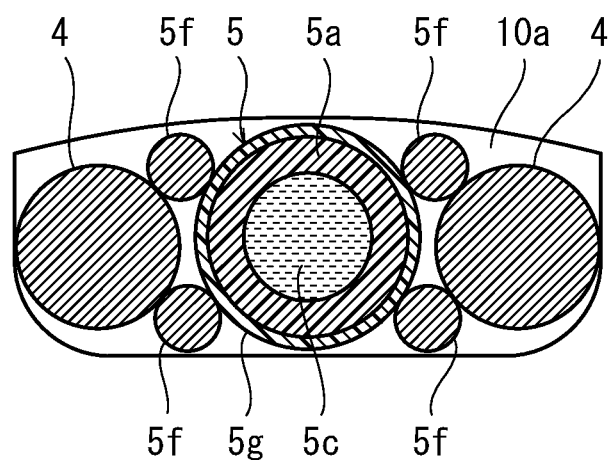

FIG. 12A is a sectional view showing another variation of the pressing portion 5 of the bending mechanism. The sectional view schematically shows part of a cross section perpendicular to the axial direction of the shaft part 1. FIG. 12B shows a comparative example compared to FIG. 12A. As shown in FIG. 12A, the pressing portion 5 of the present variation and the pressing portion 5 of Embodiment 2 (see FIG. 8) share the following common features: the feature that the cross-sectional shape of the groove 10a is substantially rectangular; and the feature that two operating rods 4 are disposed on both sides of the tube 5a, respectively. However, the pressing portion 5 of the present variation is different from the pressing portion 5 of Embodiment 2 in the following point: in the pressing portion 5 of the present variation, the outer shape of the cross section of the tube 5a is rectangular corresponding to the cross-sectional shape of the groove 10a, whereas the inner shape of the cross section of the tube 5a is circular.

On the other hand, as shown in FIG. 12B, the pressing portion 5 of the comparative example is different from the pressing portion 5 of the present variation (see FIG. 12A) in the following point: in the pressing portion 5 of the comparative example, the outer shape and the inner shape of the cross section of the tube 5a are both circular, and four spacer rods 5f are arranged around the tube 5a. A thermally shrinkable tube 5g is provided around the tube 5a. The base end portion of the tube 5a is connected to the pipe 5b made of stainless steel (SUS) (see FIG. 1, for example). The connection between the tube 5a and the pipe 5b, and the vicinity of the connection, are partly covered by the thermally shrinkable tube 5g. This makes it possible to suppress the occurrence of rapid (local) expansion at the connection between the tube 5a and the pipe 5b.

In the present variation shown in FIG. 12A, since the inner shape of the cross section of the tube 5a is circular, the thickness between the center of the inner circular shape of the tube 5a and each of the four corners of the outer rectangular shape of the tube 5a is greater than the thickness of the other parts of the tube 5a. As a result, at the time of expanding the tube 5a, the occurrence of rapid (local) expansion is suppressed at the four corners of the tube 5a, and for this reason, the tube 5a is less likely to tear. Consequently, the thermally shrinkable tube 5g used in the comparative example of FIG. 12B is no longer necessary.

It should be noted that, in the pressing portion 5 of Embodiment 2 (see FIG. 8) and the present variation (see FIG. 12), two operating rods 4 are arranged around the tube 5a. Three or more operating rods 4 may be arranged around the tube 5a. As a result, a plurality of operating rods 4 can be fixed by one tube 5a.

Other Embodiments

The end effector of the above-described embodiments is configured as medical forceps. However, the end effector is not limited to medical forceps. The end effector may be a surgical tool such as a gripper, scissors, a stapler, a needle holder, or an electric surgical knife. Further alternatively, the end effector may be an electrically driven device such as an electrosurgical electrode, a transducer, or a sensor. Still further alternatively, the end effector may be a fluid feeding nozzle for use in, for example, suction, gas insufflation, irrigation, feeding of a treatment fluid, accessory introduction, or biopsy extraction. Still further alternatively, the end effector may be mounted with an image capturing device such as a camera. The end effector is not limited to medical use, but may be applied to industrial use. For example, the end effector may be used for inspecting the inside of piping.

In the above-described embodiments, the shaft part 1 is provided with the grooves 10a, and is covered with the outer tube. The shaft part 1 may be provided with through-holes. In the above-described embodiments, the bendable part 2 is provided with the through-holes 20a. The bendable part 2 may be provided with grooves and be covered with an outer tube.

In the above-described embodiments, the pressing position is located at the distal end of the shaft part 1. The pressing position may be located at any position of the shaft part 1.

In the above-described embodiments, driving force transmission members that transmit driving force for bending the bendable part 2 are the operating rods 4. The driving force transmission members may be wires. Elongated members capable of transmitting pulling force or pushing force in the longitudinal direction thereof can be used as the driving force transmission members. The wires transmit pulling force, and the rods transmit pulling force and pushing force. Rods may be used instead of the restraining wires 8.

In the above-described embodiments, the inside of the tube 5a is filled with the hydraulic liquid 5c. The inside of the tube 5a may be filled with a working fluid that is not the hydraulic liquid 5c, but working gas. In this case, the tube 5a is supplied with not liquid pressure, but gas pressure.

In the above-described embodiments, the bendable part 2 includes a plurality of segment members 20, which are linked together to form one line in the axial direction of the bendable part 2. Instead of a series of the segment members, a spring or a rubber member can be used. As one example, in the case of using a spring, a coil spring can be used instead of the plurality of segment members 20, and the core member of the coil spring may be provided with the through-holes 20a extending in the axial direction. As another example, in the case of using a rubber member, a cylindrical rubber member can be used instead of the plurality of segment members 20, and the cylindrical rubber member may be provided with the through-holes 20a extending in the axial direction.

In the above-described embodiments, the swing axes of the segment members 20 are parallel to each other. However, the directions of the swing axes are not thus limited. For example, the segment members 20 may be divided into different groups, i.e., one group in which the swing axes of the segment members 20 are parallel to each other in one direction and another group in which the swing axes of the segment members 20 are parallel to each other in another direction different from the one direction (e.g., in a direction orthogonal to the one direction). Each of these groups is provided with the operating rods 4, and thereby the bendable part 2 is made bendable in two directions. Similarly, the bendable part 2 can be made bendable in three or more directions.

In the above-described embodiments, by expanding the tubes 5a (pressing portions 5), the operating rods 4 and/or the restraining wires 8 are pressed against the wall surfaces of the grooves 10a of the shaft part 1. The operating rods 4 and/or the restraining wires 8 may be pressed against the outer tube 11 of the shaft part 1. In short, the operating rods 4 and/or the restraining wires 8 may be required to be pressed against a fixed portion or fixed portions of the shaft part 1. The term "fixed portion" herein means a portion different from a movable portion such as the operating rod 4.

In the above-described embodiments, the forceps serving as the forward end part 3 (the end effector) are driven by the rod 7. The end effector such as the forceps may be driven by hydraulic pressure or electric power. At the time, piping or electrical wiring for feeding hydraulic pressure or electric power from the base end part to the forward end part 3 may be inserted through a hollow in the shaft part 1, the bendable part 2, or the inner tube 6. In the case of driving the forceps serving as the forward end part 3 (the end effector) by a rod, the rod may be inserted through the hollow in the shaft part 1, the bendable part 2, or the inner tube 6. The shaft part 1, the bendable part 2, and the inner tube 6 may each have a solid core. In the above-described embodiments, the forceps are driven by one rod 7. The forceps may be driven by at least two wires.

For the purpose of inhibiting wear between the operating rod 4 and the tube 5a, a highly wear-resistant member and/or a highly slidable member may be provided between the operating rod 4 and the tube 5a.

In the above-described embodiments, the adjacent segment members 20 are coupled together by a pair of pins 21. The adjacent segment members 20 may be coupled together without using the pins 21. For example, of the adjacent segment members 20, one main surface and the other main surface that face each other in the axial direction are provided with a groove and a protrusion, respectively, and the curvature of a partial circle of the cross-sectional shape of the protrusion and the curvature of a partial circle of the cross-sectional shape of the groove may be made equal to each other (not shown). In this configuration, the two main surfaces of the adjacent segment members 20 slide on each other while being in surface contact with each other, and thereby the adjacent segment members 20 rotate relative to each other.

In the above-described embodiments, the tube 5a and the pipe 5b are connected to each other by utilizing the shrinkage of the shrinkable member. The tube 5a and the pipe 5b may be connected to each other by different means, for example, by adhesion.

From the foregoing description, numerous modifications and other embodiments of the present invention are obvious to a person skilled in the art. Therefore, the foregoing description should be interpreted only as an example and is provided for the purpose of teaching the best mode for carrying out the present invention to a person skilled in the art. The structural and/or functional details may be substantially modified without departing from the spirit of the present invention.

INDUSTRIAL APPLICABILITY

The present invention is useful when applied to equipment that includes a bending mechanism.

REFERENCE SIGNS LIST 1 shaft part
2, 2A bendable part 2a proximal end (of the bendable part)
2b distal end (of the bendable part)
3 forward end part (end effector)
3a proximal end (of the forward end part)
4 operating rod
5 pressing portion
5a tube
5b pipe
5c hydraulic liquid
5d rod portion
5e enlarged portion
5f spacer rod
5g thermally shrinkable tube
6 inner tube
6a interior space
7 rod
8 restraining wire
10, 10A shaft
10a groove
10b interior space
11 outer tube
20 segment member
20a through-hole
20b interior space
21 swing pin
40 wrist rotation driver
41 bending driver
42 forward end driver
43 end effector driver
44 controller
45 display
46 operating unit
47 endoscope
100, 100A, 100B, 100C bending mechanism
200 medical equipment
201 first bendable part
202 second bendable part

The invention claimed is:

1. A bending mechanism comprising:
a shaft part;
a bendable part whose proximal end is linked to a distal end of the shaft part, the bendable part being bendable in a direction orthogonal to an axis of the shaft part;
a forward end part whose proximal end is linked to the bendable part;
an operating rod, or an operating wire, inserted through a groove or a hole of the shaft part and a groove or a hole of the bendable part, the groove or the hole of the shaft part being provided in a manner to extend along an axial direction of the shaft part, the groove or the hole of the bendable part being provided in a manner to extend along an axial direction of the bendable part, the operating rod or the operating wire having a distal end thereof fixed to the bendable part; and
a pressing portion configured to be able to press the operating rod or the operating wire against a fixed portion of the shaft part, wherein
the bendable part is configured to be bendable as a result of the operating rod or the operating wire being operated in an extending direction of the operating rod or the operating wire,
the operating rod or the operating wire is configured such that, when the operating rod or the operating wire is pressed against the fixed portion of the shaft part by the pressing portion, friction force is generated, and at a pressing position where the operating rod or the operating wire is pressed against the fixed portion of the shaft part, the operating rod or the operating wire is fixed in the axial direction by the friction force,
the pressing portion includes a tube that is inserted through the groove or the hole of the shaft part adjacently to the operating rod or the operating wire, the tube being expandable by being supplied with fluid pressure, and
the tube is configured to expand by being supplied with the fluid pressure and be able to press the operating rod or the operating wire against the fixed portion of the shaft part.

2. The bending mechanism according to claim 1, wherein the bendable part includes:
a first bendable part bendable in a first direction orthogonal to the axial direction of the shaft part; and
a second bendable part bendable in a second direction orthogonal to the axial direction of the shaft part, the second direction being different from the first direction.

3. The bending mechanism according to claim 1, wherein a plurality of the operating rods or a plurality of the operating wires are arranged around the tube.

4. The bending mechanism according to claim 1, wherein the pressing portion further includes a spacer rod inserted through the groove or the hole of the shaft part in the axial direction, the spacer rod disposed in a gap that is formed between the tube and at least one of the fixed portion of the shaft part and the operating rod or the operating wire.

5. The bending mechanism according to claim 1, wherein a cross section of the groove or the hole of the shaft part, the cross section being perpendicular to the axial direction, has a predetermined shape, and
a cross section of the tube has a shape that at least partly corresponds to the predetermined shape of the cross section of the groove or the hole.

6. The bending mechanism according to claim 5, wherein the cross section of the groove or the hole of the shaft part, the cross section being perpendicular to the axial direction, has a rectangular shape,
an outer shape of the cross section of the tube is rectangular corresponding to the shape of the cross section of the groove or the hole, and
an inner shape of the cross section of the tube is circular.

7. The bending mechanism according to claim 1, wherein the bendable part includes a plurality of segment members that are linked together to form one line in the axial direction of the bendable part,
the operating rod or the operating wire is inserted through grooves or holes of the plurality of segment members, the grooves or the holes being provided over the plurality of segment members in a manner to extend in the axial direction, and
the distal end of the operating rod or the operating wire is fixed to the segment member that is positioned at a distal end of the bendable part.

8. The bending mechanism according to claim 7, further comprising a restraining rod, or a restraining wire, inserted through the grooves or the holes of the plurality of segment members, the grooves or the holes being provided over the plurality of segment members in a manner to extend in the axial direction, the restraining rod or the restraining wire having a distal end thereof fixed to the segment member that is positioned closer to the proximal end of the bendable part than the segment member that is positioned at the distal end of the bendable part, wherein the restraining rod or the restraining wire is configured to be pressed against the fixed portion of the shaft part by the pressing portion.

9. The bending mechanism according to claim 1, wherein the fixed portion of the shaft part is a wall surface of the groove or the hole of the shaft part.

10. A medical equipment comprising the bending mechanism according to claim 1.

* * * * *